(12) United States Patent
Paruch et al.

(10) Patent No.: US 7,645,762 B2
(45) Date of Patent: *Jan. 12, 2010

(54) SUBSTITUTED PYRAZOLO[1,5-A] PYRIMIDINES AS PROTEIN KINASE INHIBITORS

(75) Inventors: Kamil Paruch, Garwood, NJ (US); Timothy J. Guzi, Chatham, NJ (US); Michael P. Dwyer, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 139 days.

This patent is subject to a terminal disclaimer.

(21) Appl. No.: 11/542,902

(22) Filed: Oct. 4, 2006

(65) Prior Publication Data
US 2007/0082902 A1    Apr. 12, 2007

Related U.S. Application Data

(60) Provisional application No. 60/724,159, filed on Oct. 6, 2005.

(51) Int. Cl.
   C07D 487/04    (2006.01)
   A61K 31/519   (2006.01)
   A61P 35/04    (2006.01)
(52) U.S. Cl. .................. 514/259.3; 544/281
(58) Field of Classification Search .......... 544/281; 514/259.3
   See application file for complete search history.

(56) References Cited

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Vippagunta et. al., Advanced Drug Delivery, 2001,, 48, 3-26.*
CAS printout, downloaded Sep. 18, 2008, pp. 1-5.*

* cited by examiner

*Primary Examiner*—Brenda L Coleman
*Assistant Examiner*—Susanna Moore
(74) *Attorney, Agent, or Firm*—Palaiyur S. Kalyanaraman

(57) ABSTRACT

In its many embodiments, the present invention provides a novel class of pyrazolo[1,5-a]pyrimidine compounds as inhibitors of protein and/or checkpoint kinases, methods of preparing such compounds, pharmaceutical compositions including one or more such compounds, methods of preparing pharmaceutical formulations including one or more such compounds, and methods of treatment, prevention, inhibition, or amelioration of one or more diseases associated with the protein or checkpoint kinases using such compounds or pharmaceutical compositions. An illustrative compound is shown below:

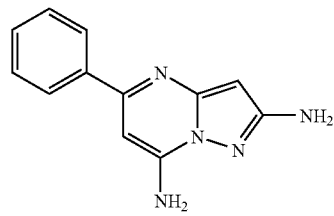

31 Claims, No Drawings

SUBSTITUTED PYRAZOLO[1,5-A] PYRIMIDINES AS PROTEIN KINASE INHIBITORS

FIELD OF THE INVENTION

The present invention relates to substituted pyrazolo[1,5-a]pyrimidine compounds useful as protein kinase inhibitors, regulators or modulators, pharmaceutical compositions containing the compounds, and methods of treatment using the compounds and compositions to treat diseases such as, for example, cancer, inflammation, arthritis, viral diseases, neurodegenerative diseases such as Alzheimer's disease, cardiovascular diseases, and fungal diseases. This application claims priority from U.S. provisional patent application Ser. No. 60/724,159 filed Oct. 6, 2005.

BACKGROUND OF THE INVENTION

Protein kinases are a family of enzymes that catalyze phosphorylation of proteins, in particular the hydroxyl group of specific tyrosine, serine, or threonine residues in proteins. Protein kinases are pivotal in the regulation of a wide variety of cellular processes, including metabolism, cell proliferation, cell differentiation, and cell survival. Uncontrolled proliferation is a hallmark of cancer cells, and can be manifested by a deregulation of the cell division cycle in one of two ways—making stimulatory genes hyperactive or inhibitory genes inactive. Protein kinase inhibitors, regulators or modulators alter the function of kinases such as cyclin-dependent kinases (CDKs), mitogen activated protein kinase (MAPK/ERK), glycogen synthase kinase 3 (GSK3beta), Chk kinases, AKT kinases and the like. Examples of protein kinase inhibitors are described in WO02/22610 A1 and by Y. Mettey et al in *J. Med. Chem.*, (2003) 46 222-236.

The cyclin-dependent kinases are serine/threonine protein kinases, which are the driving force behind the cell cycle and cell proliferation. Misregulation of CDK function occurs with high frequency in many important solid tumors. Individual CDK's, such as, CDK1, CDK2, CDK3, CDK4, CDK5, CDK6 and CDK7, CDK8 and the like, perform distinct roles in cell cycle progression and can be classified as either G1, S, or G2M phase enzymes. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over- or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development of cancer treatments.

A number of adenosine 5'-triphosphate (ATP) competitive small organic molecules as well as peptides have been reported in the literature as CDK inhibitors for the potential treatment of cancers. U.S. Pat. No. 6,413,974, col. 1, line 23-col. 15, line 10 offers a good description of the various CDKs and their relationship to various types of cancer. Flavopiridol (shown below) is a nonselective CDK inhibitor that is currently undergoing human clinical trials, A. M. Sanderowicz et al, *J. Clin. Oncol.* (1998) 16, 2986-2999.

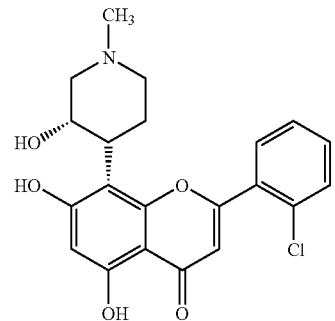

Other known inhibitors of CDKs include, for example, olomoucine (J. Vesely et al, *Eur. J. Biochem.*, (1994) 224, 771-786) and roscovitine (I. Meijer et al, *Eur. J. Biochem.*, (1997) 243, 527-536). U.S. Pat. No. 6,107,305 describes certain pyrazolo[3,4-b]pyridine compounds as CDK inhibitors. An illustrative compound from the '305 patent is:

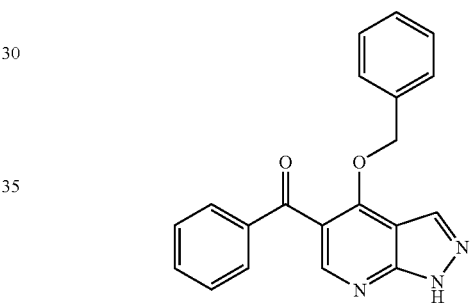

K. S. Kim et al, *J. Med. Chem.* 45 (2002) 3905-3927 and WO 02/10162 disclose certain aminothiazole compounds as CDK inhibitors.

Pyrazolopyrimidines are known. For example, WO92/18504, WO02/50079, WO95/35298, WO02/40485, EP94304104.6, EP0628559 (equivalent to U.S. Pat. Nos. 5,602,136, 5,602,137 and 5,571,813), U.S. Pat. No. 6,383,790, *Chem. Pharm. Bull.*, (1999) 47 928, *J. Med. Chem.*, (1977) 20, 296, *J. Med. Chem.*, (1976) 19 517 and *Chem. Pharm. Bull.*, (1962) 10 620 disclose various pyrazolopyrimidines. Other publications of interest include: U.S. Pat. Nos. 5,688,949 and 6,313,124, WO 98/54093, WO 03/101993, WO 03/091256, WO 04/089416 and DE 10223917.

Another series of protein kinases are those that play an important role as a checkpoint in cell cycle progression. Checkpoints prevent cell cycle progression at inappropriate times, such as in response to DNA damage, and maintain the metabolic balance of cells while the cell is arrested, and in some instances can induce apoptosis (programmed cell death) when the requirements of the checkpoint have not been met. Checkpoint control can occur in the G1 phase (prior to DNA synthesis) and in G2, prior to entry into mitosis.

One series of checkpoints monitors the integrity of the genome and, upon sensing DNA damage, these "DNA damage checkpoints" block cell cycle progression in G.sub.1 & G.sub.2 phases, and slow progression through S phase. This action enables DNA repair processes to complete their tasks before replication of the genome and subsequent separation of this genetic material into new daughter cells takes place. Inactivation of CHK1 has been shown to transduce signals from the DNA-damage sensory complex to inhibit activation of the cyclin B/Cdc2 kinase, which promotes mitotic entry, and abrogate $G_2$ arrest induced by DNA damage inflicted by either anticancer agents or endogenous DNA damage, as well as result in preferential killing of the resulting checkpoint defective cells. See, e.g., Peng et al., *Science,* 277, 1501-1505 (1997); Sanchez et al., Science, 277, 1497-1501 (1997), Nurse, *Cell,* 91, 865-867 (1997); Weinert, *Science,* 277, 1450-1451 (1997); Walworth et al., Nature, 363, 368-371 (1993); and Al-Khodairy et al., *Molec. Biol.* Cell., 5, 147-160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as CDS1/CHK2, a kinase recently discovered to cooperate with CHK1 in regulating S phase progression (see Zeng et al., Nature, 395, 507-510 (1998); Matsuoka, *Science,* 282, 1893-1897 (1998)), could provide valuable new therapeutic entities for the treatment of cancer.

Another group of kinases are the tyrosine kinases. Tyrosine kinases can be of the receptor type (having extracellular, transmembrane and intracellular domains) or the non-receptor type (being wholly intracellular). Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3 and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, IR, and IR-R. The PDGF subfamily includes the PDGF-alpha and beta receptors, CSFIR, c-kit and FLK-II. The FLK family is comprised of the kinase insert domain receptor (KDR), fetal liver kinase-1 (FLK-1), fetal liver kinase4 (FLK4) and the fms-like tyrosine kinase-1 (flt-1). For detailed discussion of the receptor-type tyrosine kinases, see Plowman et al., DN&P 7(6): 334-339, 1994.

At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene,* 8, 2025-2031 (1993). The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993).

In addition to its role in cell-cycle control, protein kinases also play a crucial role in angiogenesis, which is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. On the other hand, unwanted angiogenesis is a hallmark of several diseases, such as retinopathies, psoriasis, rheumatoid arthritis, age-related macular degeneration, and cancer (solid tumors). Protein kinases which have been shown to be involved in the angiogenic process include three members of the growth factor receptor tyrosine kinase family; VEGF-R2 (vascular endothelial growth factor receptor 2, also known as KDR (kinase insert domain receptor) and as FLK 1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al, *Cancer Research,* 56, 3540-3545 (1996)), as has been shown with mutants of VEGF-R2 which fail to mediate signal transduction. Millauer et al, Cancer Research, 56, 1615-1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGFR binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research,* 57, 3924-3928 (1997). Unlike VEGF-R2, however, FGF-R is expressed in a number of different cell types throughout the body and may or may not play important roles in other normal physiological processes in the adult. Nonetheless, systemic administration of a small molecule inhibitor of the kinase activity of FGF-R has been reported to block bFGF-induced angiogenesis in mice without apparent toxicity. Mohammad et al., *EMBO Journal,* 17, 5996-5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., Science, 277, 55-60 (1997).

Pim-1 is a small serine/threonine kinase. Elevated expression levels of Pim-1 have been detected in lymphoid and myeloid malignancies, and recently Pim-1 was identified as a prognostic marker in prostate cancer. K. Peltola, "Signaling in Cancer: Pim-1 Kinase and its Partners", Annales Universitatis Turkuensis, Sarja-Ser. D Osa-Tom. 616, (Aug. 30, 2005), http://kirjasto.utu.fi/julkaisupalvelut/annaalit/2004/D616.html. Pim-1 acts as a cell survival factor and may prevent apoptosis in malignant cells. K. Petersen Shay et al., *Molecular Cancer Research* 3:170-181 (2005).

There is a need for effective inhibitors of protein kinases in order to treat or prevent disease states associated with abnormal cell proliferation. Moreover, it is desirable for kinase inhibitors to possess both high affinity for the target kinase as well as high selectivity versus other protein kinases. Small-molecule compounds that may be readily synthesized and are potent inhibitors of cell proliferation are those, for example, that are inhibitors of one or more protein kinases, such as CHK1, CHK2, VEGF, CDKs or CDK/cyclin complexes and both receptor and non-receptor tyrosine kinases.

SUMMARY OF THE INVENTION

In its many embodiments, the present invention provides substituted pyrazolo[1,5-a]pyrimidine compounds, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the protein kinases using such compounds or pharmaceutical compositions.

In one aspect, the present invention provides compounds represented by the structural formula (I):

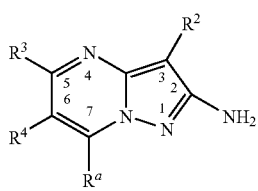

(I)

or a pharmaceutically acceptable salt, solvate, ester, or prodrug of the compound of Formula (I), wherein:

$R^2$ is selected from the group consisting of H, alkyl, cycloalkyl, cycloalkylalkyl, haloalkyl, alkenyl, alkynyl, alkenylalkyl, alkynylalkyl, heterocyclyl, heterocycloalkyl, trifluoromethyl, halo, —CN, —OCF$_3$, —CO$_2$R$^8$, —CONR$^8$R$^9$, —OR$^{8a}$, —SR$^8$, —SO$_2$R$^8$, —SO$_2$NR$^8$R$^9$, —NR$^8$SO$_2$R$^9$, —NR$^8$COR$^9$, and —NR$^8$CONR$^8$R$^9$;

$R^3$ is selected from the group consisting of haloalkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl, —NR$^5$R$^{8a}$, —NR$^8$COR$^9$, —NR$^8$SO$_2$R$^9$, —COR$^8$, —CO$_2$R$^8$, —CONR$^8$R$^9$, —CH$_2$OR$^8$, —OR$^{8b}$, —SR$^8$, —SO$_2$R$^8$, —S(O$_2$)NR$^8$R$^9$, —S(O$_2$)aryl, —S(O$_2$)heteroaryl, —C(O)NR$^8$R$^9$, —C(O)OR$^9$, —C(O)aryl, —C(O)heteroaryl, —(CHR$^5$)$_n$-aryl, —(CHR$^5$)$_n$-heteroaryl,

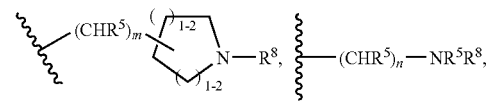

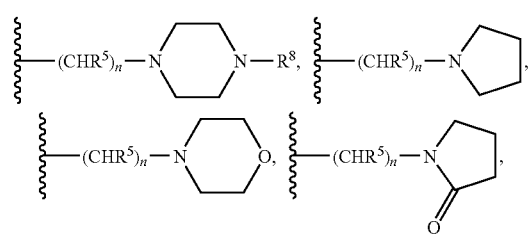

-continued

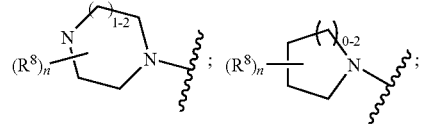

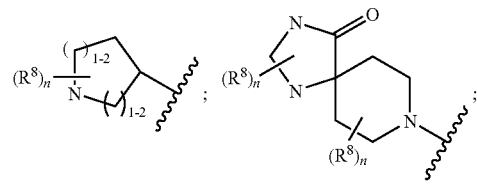

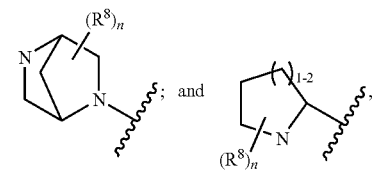

wherein each of the alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl and the heterocyclic moieties shown immediately above for $R^3$ can be unsubstituted or optionally substituted with one or more moieties which can be the same or different, each moiety being independently selected from the group consisting of H, halo, alkyl, trifluoromethyl, —OR$^8$, —NR$^8$R$^9$, —SR$^8$, —SO$_2$R$^9$, —CN, —SO$_2$NR$^8$R$^9$, —CF$_3$, and —NO$_2$.;

$R^4$ is selected from the group consisting of H, halo, haloalkyl, alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl, —NR$^8$R$^9$, —NR$^8$COR$^9$, —NR$^8$SO$_2$R$^9$, —COR$^8$, —CO$_2$R$^8$, —CONR$^8$R$^9$, —CH$_2$OR$^8$, —OR$^8$, —SR$^8$, —SO$_2$R$^8$, —S(O$_2$)NR$^8$R$^9$, —S(O$_2$)aryl, —S(O$_2$)heteroaryl, —C(O)OR$^9$, —C(O)aryl, —C(O)heteroaryl, —(CHR$^5$)$_n$-aryl, —(CHR$^5$)$_n$-heteroaryl,

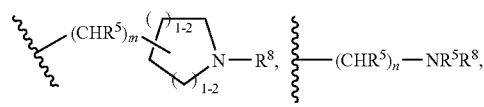

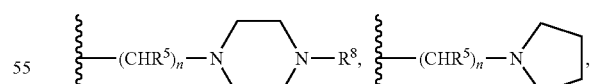

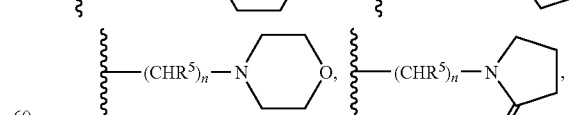

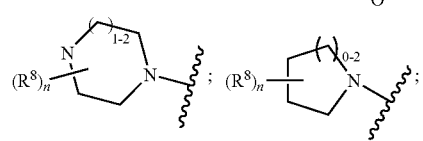

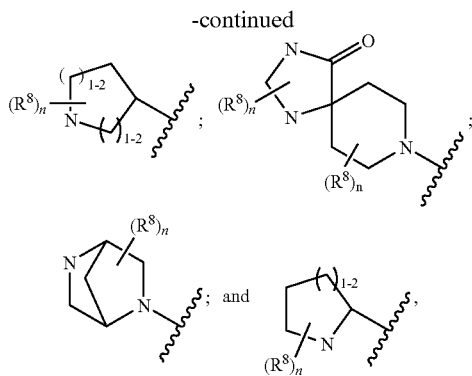

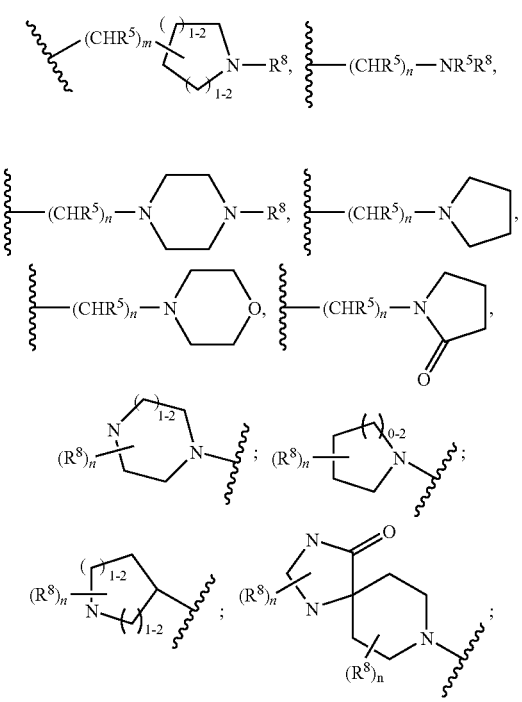

wherein each of the alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl and the heterocyclic moieties shown immediately above for $R^4$ can be unsubstituted or optionally substituted with one or more moieties which can be the same or different, each moiety being independently selected from the group consisting of H, halo, alkyl, trifluoromethyl, —$OR^8$, —$NR^8R^9$, —$SR^8$, —$SO_2R^9$, —CN, —$SO_2NR^8R^9$, —$CF_3$, and —$NO_2$;

$R^a$ is selected from the group consisting of H, halo, haloalkyl, alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl, —$NR^8R^9$, —$NR^8COR^9$, —$NR^8SO_2R^9$, —$COR^8$, —$CO_2R^8$, —$CONR^8R^9$, —$CH_2R^8$, —$OR^8$, —$SR^8$, —$SO_2R^8$, —$S(O_2)NR^8R^9$, —$S(O_2)$aryl, —$S(O_2)$heteroaryl, —$C(O)OR^9$, —$C(O)$aryl, —$C(O)$heteroaryl, —$(CHR^5)_n$-aryl, —$(CHR^5)_n$-heteroaryl,

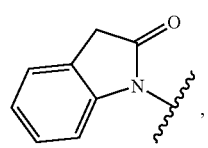

wherein each of the alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl and the heterocyclic moieties shown immediately above for $R^a$ can be unsubstituted or optionally substituted with one or more moieties which can be the same or different, each moiety being independently selected from the group consisting of H, halo, alkyl, trifluoromethyl, —$OR^8$, —$NR^8R^9$, —$SR^8$, —$SO_2R^9$, —CN, —$SO_2NR^8R^9$, —$CF_3$, and —$NO_2$;

$R^5$ is selected from the group consisting of H, alkyl, aryl or cycloalkyl;

$R^6$ is selected from the group consisting of H, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —$CF_3$, —$OCF_3$, —CN, —$OR^5$, —$NR^5R^{10}$, —$C(R^5R^{11})_p$—$R^9$, —$N(R^5)Boc$, —$(CR^5R^{11})_p OR^5$, —$C(O_2)R^5$, —$C(O)R^5$, —$C(O)NR^5R^{10}$, —$SO_3H$, —$SR^{10}$, —$S(O_2)R^7$, —$S(O_2)NR^5R^{10}$, —$N(R^5)S(O_2)R^7$, —$N(R^5)C(O)R^7$ and —$N(R^5)C(O)NR^5R^{10}$;

$R^7$ is selected from the group consisting of alkyl, cycloalkyl, aryl, arylalkenyl, heteroaryl, arylalkyl, heteroarylalkyl, heteroarylalkenyl, and heterocyclyl, wherein each of the alkyl, cycloalkyl, heteroarylalkyl, aryl, arylalkenyl, heteroaryl, arylalkyl, heteroarylalkyl, heteroarylalkenyl, and heterocyclyl can be unsubstituted or optionally independently substituted with one or more moieties which can be the same or different, each moiety being independently selected from the group consisting of halo, alkyl, aryl, cycloalkyl, $CF_3$, $OCF_3$, CN, —$OR^5$, —$NR^5R^{10}$, —$CH_2OR^5$, —$C(O_2)R^5$, —$C(O)NR^5R^{10}$, —$C(O)R^5$, —$SR^{10}$, —$S(O_2)R^{10}$, —$S(O_2)NR^5R^{10}$, —$N(R^5)S(O_2)R^{10}$, —$N(R^5)C(O)R^{10}$ and —$N(R^5)C(O)NR^5R^{10}$;

$R^8$ is selected from the group consisting of H, —$OR^6$, —$NR^5R^6$, —$C(O)NR^5R^{10}$, —$S(O_2)NR^5R^{10}$, —$C(O)R^7$, —$C(=N-CN)-NH_2$, —$C(=NH)-NHR^5$, heterocyclyl, —$S(O_2)R^7$, —OR10, —$CF_3$, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —CF$_3$, —OCF$_3$, —CN, —OR$^5$, —NR$^5$R$^{10}$, —C(R$^5$R$^{11}$)$_p$—R$^9$, —N(R$^5$)Boc, —(CR$^5$R$^{11}$)$_p$OR$^5$, —C(O$_2$)R$^5$, —C(O)R$^5$, —C(O)NR$^5$R$^{10}$, —SO$_3$H, —SR$^{10}$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$R$^{10}$;

R$^{8a}$ is selected from the group consisting of —OR$^6$, —NR$^5$R$^6$, —C(O)NR$^5$R$^{10}$, —S(O$_2$)NR$^5$R$^{10}$, —C(O)R$^7$, —C(=N—CN)—NH$_2$, —C(=NH)—NHR$^5$, heterocyclyl, —S(O$_2$)R$^7$,

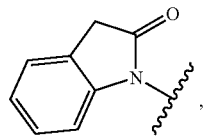

—OR$^{10}$, —CF$_3$, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —CF$_3$, —OCF$_3$, —CN, —OR$^5$, —NR$^5$R$^{10}$, —C(R$^5$R$^{11}$)$_p$—R$^9$, —N(R$^5$)Boc, —(CR$^5$R$^{11}$)$_p$OR$^5$, —C(O$_2$)R$^5$, —C(O)R$^5$, —C(O)NR$^5$R$^{10}$, —SO$_3$H, —SR$^{10}$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$R$^{10}$;

R$^{8b}$ is selected from the group consisting of —OR$^6$, —NR$^5$R$^6$, —C(O)NR$^5$R$^{10}$, —S(O$_2$)NR$^5$R$^{10}$, —C(O)R$^7$, —C(=N—CN)—NH$_2$, —C(=NH)—NHR$^5$, heterocyclyl, —S(O$_2$)R$^7$,

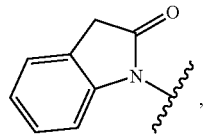

—OR$^{10}$, —CF$_3$, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —CF$_3$, —OCF$_3$, —CN, —OR$^5$, —NR$^5$R$^{10}$, —C(R$^5$R$^{11}$)$_p$—R$^9$, —N(R$^5$)Boc, —(CR$^5$R$^{11}$)$_p$OR$^5$, —C(O$_2$)R$^5$, —C(O)R$^5$, —C(O)NR$^5$R$^{10}$, —SO$_3$H, —SR$^{10}$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$R$^{10}$;

R$^9$ is selected from the group consisting of H, —OR$^6$, —NR$^5$R$^6$, —C(O)NR$^5$R$^{10}$, —S(O$_2$)NR$^5$R$^{10}$, —C(O)R$^7$, —C(=N—CN)—NH$_2$, —C(=NH)—NHR$^5$, heterocyclyl, —S(O$_2$)R$^7$,

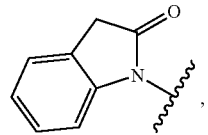

—OR$^{10}$, —CF$_3$, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —CF$_3$, —OCF$_3$, —CN, —OR$^5$, —NR$^5$R$^{10}$, —C(R$^5$R$^{11}$)$_p$—R$^9$, —N(R$^5$)Boc, —(CR$^5$R$^{11}$)$_p$OR$^5$, —C(O$_2$)R$^5$, —C(O)R$^5$, —C(O)NR$^5$R$^{10}$, —SO$_3$H, —SR$^{10}$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$R$^{10}$;

R$^{10}$ is selected from the group consisting of H, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —CF$_3$, —OCF$_3$, —CN, —OR$^5$, —NR$^5$R$^{11}$, —C(R$^5$R$^{11}$)$_p$—R$^9$, —N(R$^5$)Boc, —(CR$^5$R$^{11}$)$_p$OR$^5$, —C(O$_2$)R$^5$, —C(O)R$^5$, —C(O)NR$^5$R$^{11}$, —SO$_3$H, —SR$^{10}$, —S(O$_2$)R$^7$, —S(O$_2$)NR$^5$R$^{11}$, —N(R$^5$)S(O$_2$)R$^7$, —N(R$^5$)C(O)R$^7$ and —N(R$^5$)C(O)NR$^5$R$^{11}$;

or optionally (i) R$^5$ and R$^{11}$ in the moiety —NR$^5$R$^{11}$, or (ii) R$^5$ and R$^6$ in the moiety —NR$^5$R$^6$, may be joined together to form a cycloalkyl or heterocyclyl moiety, with each of the cycloalkyl or heterocyclyl moiety being unsubstituted or optionally independently being substituted with one or more R$^9$ groups; and R$^{11}$ is H, halo or alkyl;

m is 0 to 4;

n is 1 to 4; and p is 1 to 4, with the following provisos:

(a) When R$^2$ is as defined above, then at least one of R$^3$, R$^4$ and R$^a$ is selected from the group consisting of —NH$_2$, —OH, alkoxy, alkylthio, halo, alkynyl, alkenylalkyl, and alkynylalkyl; or (b) When R$^3$, R$^4$ and R$^a$ are as defined above, then R$^2$ is selected from the group consisting of alkyl, cycloalkyl, cycloalkylalkyl, haloalkyl, alkenyl, alkynyl, alkenylalkyl, alkynylalkyl, trifluoromethyl, —OCF$_3$, —OR$^{8a}$, —SR$^8$, and —NR$^8$CONR$^8$R$^9$.

The compounds of Formula I can be useful as protein kinase inhibitors and can be useful in the treatment and prevention of proliferative diseases, for example, cancer, inflammation and arthritis, neurodegenerative diseases such Alzheimer's disease, cardiovascular diseases, viral diseases and fungal diseases.

DETAILED DESCRIPTION

The present invention provides substituted pyrazolo[1,5-a]pyrimidine compounds which are represented by structural Formula I, or pharmaceutically acceptable salts, solvates, esters, or prodrugs thereof, wherein the various moieties are as described above.

Referring to Formula (I) above, in some embodiments, $R^2$ is H.

In other embodiments, $R^2$ is Br.

In other embodiments, $R^2$ is selected from the group consisting of Cl, —SH, —CN, alkyl, alkenyl, alkynyl, and cyclopropyl.

In other embodiments, $R^2$ is selected from the group consisting of cycloalkyl, cycloalkylalkyl, heterocyclyl, heterocycloalkyl, —OCF$_3$, —CO$_2$R$^8$, —CONR$^8$R$^9$, —OR$^{8a}$, —SR$^8$, —SO$_2$R$^8$, —SO$_2$NR$^8$R$^9$, —NR$^8$SO$_2$R$^9$, —NR$^8$COR$^9$, and —NR$^8$CONR$^8$R$^9$.

In some embodiments, $R^3$ is benzyl.

In other embodiments, $R^3$ is methyl.

In other embodiments, $R^3$ is selected from the group consisting of aryl, arylalkyl, arylalkenyl, cycloalkyl, cycloalkylalkyl, heterocyclyl, heterocyclylalkyl, heteroaryl, heteroarylalkyl, —S(O$_2$)aryl, —S(O$_2$)heteroaryl, —C(O)aryl, —C(O)heteroaryl, —(CHR$^5$)$_n$-aryl, —(CHR$^5$)$_n$-heteroaryl,

[chemical structures]

wherein each of the aryl, arylalkyl, arylalkenyl, cycloalkyl, cycloalkylalkyl, heterocyclyl, heterocyclylalkyl, heteroaryl, heteroarylalkyl and the heterocyclic moieties shown immediately above for $R^3$ can be unsubstituted or optionally substituted with one or more moieties which can be the same or different, each moiety being independently selected from the group consisting of H, halo, alkyl, trifluoromethyl, —OR$^8$, —NR$^8$R$^9$, —SR$^8$, —SO$_2$R$^9$, —CN, —SO$_2$NR$^8$R$^9$, —CF$_3$, and —NO$_2$.

In other embodiments, $R^3$ is selected from the group consisting of haloalkyl, alkenyl, alkynyl, alkenylalkyl, alkynylalkyl, —NR$^5$R$^{8a}$, —NR$^8$COR$^9$, —NR$^8$SO$_2$R$^9$, —COR$^8$, —CO$_2$R$^8$, —CONR$^8$R$^9$, —CH$_2$OR$^8$, OR$^{8b}$, —SR$^8$, —SO$_2$R$^8$, —S(O$_2$)NR$^8$R$^9$, wherein each of the alkyl, alkenyl, alkynyl, alkenylalkyl, alkynylalkyl, can be unsubstituted or optionally substituted with one or more moieties which can be the same or different, each moiety being independently selected from the group consisting of H, halo, alkyl, trifluoromethyl, —OR$^8$, —NR$^8$R$^9$, —SR$^8$, —SO$_2$R$^9$, —CN, —SO$_2$NR$^8$R$^9$, —CF$_3$, and —NO$_2$.

In other embodiments, $R^3$ is alkoxy.

In other embodiments, $R^3$ is alkylthio.

In other embodiments, $R^3$ is selected from the group consisting of

[chemical structures]

In other embodiments, $R^3$ is aryl substituted with 1-3 aryl or heteroaryl groups which can be the same or different and are each independently selected from the group consisting of phenyl, pyridyl, thiophenyl, furanyl and thiazolo groups.

In other embodiments, $R^3$ is heteroaryl substituted with 1-3 aryl or heteroaryl groups which can be the same or different and are each independently selected from the group consisting of phenyl, pyridyl, thiophenyl, furanyl and thiazolo groups.

In other embodiments, $R^3$ is selected from the group consisting of heteroaryl, heteroarylalkyl, heterocyclyl and heterocyclylalkyl.

In some embodiments, $R^3$ is phenyl.

In some embodiments, $R^4$ is H.

In other embodiments, $R^4$ is selected from the group consisting of Cl, Br, —OH, —SH, alkyl, alkenyl, alkynyl, haloalkyl and cyclopropyl.

In other embodiments, $R^4$ is —NH$_2$.

In other embodiments, $R^4$ is —OH.

In other embodiments, $R^4$ is alkoxy.

In other embodiments, $R^4$ is alkylthio.

In other embodiments, $R^4$ is halo.

In some embodiments, $R^a$ is —NH$_2$.

In other embodiments, $R^a$ is —OH.

In other embodiments, $R^a$ is alkoxy.

In other embodiments, $R^a$ is alkylthio.

In other embodiments, $R^a$ is halo.

In other embodiments, $R^a$ is Cl.

In some embodiments, $R^5$ is H.

In some embodiments, n is 1.

In some embodiments, p is 1.

Non-limiting examples of compounds of Formula (I) include:

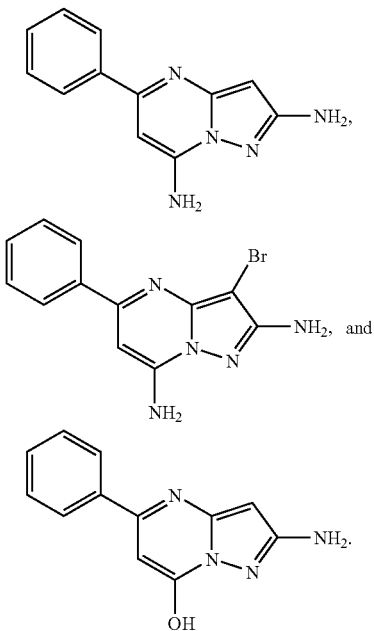

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl).

Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

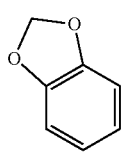 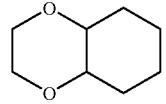 and 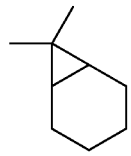

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

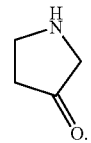

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

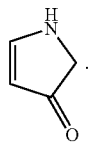

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

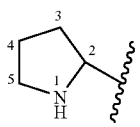

there is no —OH attached directly to carbons marked 2 and 5.

It should also be noted that tautomeric forms such as, for example, the moieties:

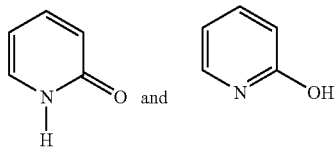

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy$(C_1-C_6)$alkyl, amino $(C_1-C_4)$alkyl or mono-N— or di-N,N—$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

The compounds according to the invention can have pharmacological properties; in particular, the compounds of Formula (I) can be inhibitors, regulators or modulators of protein kinases. Non-limiting examples of protein kinases that can be inhibited, regulated or modulated include cyclin-dependent kinases (CDKs), such as, CDK1, CDK2, CDK3, CDK4, CDK5, CDK6, CDK7, and CDK8, mitogen activated protein kinase (MAPK/ERK), glycogen synthase kinase 3 (GSK3beta), Chk kinases, such as Chk1 and Chk2, Pim-1 kinases, tyrosine kinases, such as the HER subfamily (including, for example, EGFR (HER1), HER2, HER3 and HER4), the insulin subfamily (including, for example, INS-R, IGF-IR, IR, and IR-R), the PDGF subfamily (including, for example, PDGF-alpha and beta receptors, CSFIR, c-kit and FLK-II), the FLK family (including, for example, kinase insert domain receptor (KDR), fetal liver kinase-1 (FLK-1), fetal liver kinase4 (FLK4) and the fms-like tyrosine kinase-1 (flt-1)), non-receptor protein tyrosine kinases, for example LCK, Src, Frk, Btk, Csk, Abl, Zap70, Fes/Fps, Fak, Jak, Ack, and LIMK, growth factor receptor tyrosine kinases such as VEGF-R2, FGF-R, TEK, Akt kinases and the like.

The compounds of Formula (I) can be inhibitors of protein kinases such as, for example, the inhibitors of the checkpoint kinases such as Chk1, Chk2 and the like. Preferred compounds can exhibit $IC_{50}$ values of less than about 25 μm, preferably about 0.001 to about 1.0 μm, and more preferably about 0.001 to about 0.1 μm. The assay methods are described in the Examples set forth below.

The compounds of Formula (I) can be inhibitors of protein kinases such as, for example, the cyclin-dependent kinases such as CDK1, CDK2, CDK3, CDK4, CDK5, CDK6, CDK7, and CDK8, and the like. The compounds shown in Table 1 exhibited CDK2 inhibitory activity ($IC_{50}$) of about 0.0001 μM to >about 5 μM. The assay methods are described in the examples below.

TABLE 1

| Structure | CDK2 $IC_{50}$ (μM) |
|---|---|
| 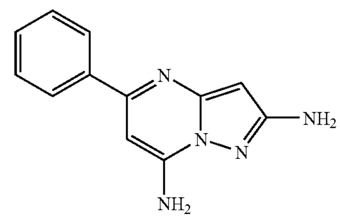 | 0.08 |
| 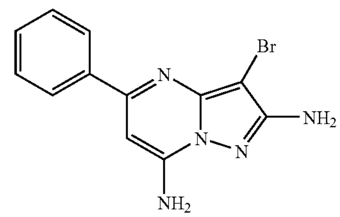 | 4.67 |

The compounds of Formula (I) can be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974 cited earlier, incorporated by reference herein.

More specifically, the compounds of Formula (I) can be useful in the treatment of a variety of cancers, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formula (I) may also be useful in the treatment of Alzheimer's disease, as suggested by the recent finding that CDK5 is involved in the phosphorylation of tau protein (*J. Biochem*, (1995) 117, 741-749).

Compounds of Formula (I) may induce or inhibit apoptosis. The apoptotic response is aberrant in a variety of human diseases. Compounds of Formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formula (I), as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formula (I) may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formula (I) may also be useful in inhibiting tumor angiogenesis and metastasis.

Compounds of Formula (I) may also act as inhibitors of other protein kinases, e.g., protein kinase C, her2, raf 1, MEK1, MAP kinase, EGF receptor, PDGF receptor, IGF receptor, PI3 kinase, wee1 kinase, Src, Abl and thus be effective in the treatment of diseases associated with other protein kinases.

Another aspect of this invention is a method of treating a mammal (e.g., human) having a disease or condition associated with the CDKs by administering a therapeutically effective amount of at least one compound of Formula (I), or a pharmaceutically acceptable salt, solvate, ester, or prodrug of the compound to the mammal.

A preferred dosage is about 0.001 to 500 mg/kg of body weight/day of the compound of Formula (I). An especially preferred dosage is about 0.01 to 25 mg/kg of body weight/day of a compound of Formula (I), or a pharmaceutically acceptable salt, solvate, ester, or prodrug of the compound.

The compounds of this invention may also be useful in combination (administered together or sequentially) with one or more of anti-cancer treatments such as radiation therapy, and/or one or more anti-cancer agents different from the compound of Formula (I). The compounds of the present invention can be present in the same dosage unit as the anti-cancer agent or in separate dosage units.

Another aspect of the present invention is a method of treating one or more diseases associated with cyclin dependent kinase, comprising administering to a mammal in need of such treatment an amount of a first compound, which is a compound of Formula (I), or a pharmaceutically acceptable salt, solvate, ester, or prodrug thereof; and an amount of at least one second compound, the second compound being an anti-cancer agent different from the compound of Formula (I), wherein the amounts of the first compound and the second compound result in a therapeutic effect.

Non-limiting examples of suitable anti-cancer agents include cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™(4-[2-[4-[(11R)-3,10-dibromo-8-chloro-6,11-dihydro-5H-benzo[5,6]cyclohepta[1,2-b]pyridin-11-yl-]-1-piperidinyl]-2-oxoehtyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Ifosfomide, Rituximab, C225, and Campath.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Compounds of Formula (I) may also be administered sequentially with known anticancer or cytotoxic agents when a combination formulation is inappropriate. The invention is not limited in the sequence of administration; compounds of Formula (I) may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in an aspect, this invention includes combinations comprising an amount of at least one compound of Formula (I), or a pharmaceutically acceptable salt, solvate, ester, or prodrug thereof, and an amount of one or more anti-cancer treatments and anti-cancer agents listed above wherein the amounts of the compounds/treatments result in desired therapeutic effect.

A method of inhibiting one or more Checkpoint kinases in a patient in need thereof, comprising administering to the patient a therapeutically effective amount of at least one compound of Formula (I) or a pharmaceutically acceptable salt, solvate, ester, or prodrug thereof.

Another aspect of the present invention is a method of treating, or slowing the progression of, a disease associated with one or more Checkpoint kinases in a patient in need thereof, comprising administering a therapeutically effective amount of at least one compound of Formula (I) or a pharmaceutically acceptable salt, solvate, ester, or prodrug thereof.

Yet another aspect of the present invention is a method of treating one or more diseases associated with Checkpoint kinases, comprising administering to a mammal in need of such treatment an amount of a first compound, which is a compound of Formula (I), or a pharmaceutically acceptable salt, solvate, ester, or prodrug thereof; and an amount of at least one second compound, the second compound being an anti-cancer agent, wherein the amounts of the first compound and the second compound result in a therapeutic effect.

Another aspect of the present invention is a method of treating, or slowing the progression of, a disease associated with one or more Checkpoint kinases in a patient in need thereof, comprising administering a therapeutically effective amount of a pharmaceutical composition comprising in combination at least one pharmaceutically acceptable carrier and at least one compound according to Formula (I), or a pharmaceutically acceptable salt, solvate, ester, or prodrug thereof.

In the above methods, the checkpoint kinase to be inhibited can be Chk1 and/or Chk2.

Another aspect of the present invention is a method of inhibiting one or more tyrosine kinases in a patient in need thereof, comprising administering to the patient a therapeutically effective amount of at least one compound of Formula (I) or a pharmaceutically acceptable salt, solvate, ester, or prodrug thereof.

Yet another aspect of the present invention is a method of treating, or slowing the progression of, a disease associated with one or more of Akt kinases, Aurora kinase, and tyrosine kinases in a patient in need thereof, comprising administering a therapeutically effective amount of at least one compound of Formula (I) or a pharmaceutically acceptable salt, solvate, ester, or prodrug thereof.

Another aspect of the present invention is a method of treating one or more diseases associated with Akt kinases, Aurora kinases and/or tyrosine kinases, comprising administering to a mammal in need of such treatment an amount of a first compound, which is a compound of Formula (I), or a pharmaceutically acceptable salt, solvate, ester, or prodrug thereof; and an amount of at least one second compound, the second compound being an anti-cancer agent, wherein the amounts of the first compound and the second compound result in a therapeutic effect.

Another aspect of the present invention is a method of treating, or slowing the progression of, a disease associated with one or more of Akt kinases, Aurora kinases and tyrosine kinases in a patient in need thereof, comprising administering a therapeutically effective amount of a pharmaceutical composition comprising in combination at least one pharmaceutically acceptable carrier and at least one compound of Formula (I) or a pharmaceutically acceptable salt, solvate, ester, or prodrug thereof.

In the above methods, the tyrosine kinase can be VEGFR, EGFR, HER2, SRC, JAK and/or TEK.

Yet another aspect of the present invention is a method of treating, or slowing the progression of, a disease associated with Pim-1 kinases in a patient in need thereof, comprising administering a therapeutically effective amount of at least one compound of Formula (I) or a pharmaceutically acceptable salt, solvate, ester, or prodrug thereof.

Another aspect of the present invention is a method of treating one or more diseases associated with Pim-1 kinases, comprising administering to a mammal in need of such treatment an amount of a first compound, which is a compound of Formula (I), or a pharmaceutically acceptable salt, solvate, ester, or prodrug thereof; and an amount of at least one second compound, the second compound being an anti-cancer agent, wherein the amounts of the first compound and the second compound result in a therapeutic effect.

Another aspect of the present invention is a method of treating, or slowing the progression of, a disease associated with Pim-1 kinases in a patient in need thereof, comprising administering a therapeutically effective amount of a pharmaceutical composition comprising in combination at least one pharmaceutically acceptable carrier and at least one compound of Formula (I) or a pharmaceutically acceptable salt, solvate, ester, or prodrug thereof.

The pharmacological properties of the compounds of this invention may be confirmed by a number of pharmacological assays. The exemplified pharmacological assays which are described herein below have been carried out with compounds according to the invention and their salts.

This invention is also directed to pharmaceutical compositions which comprise at least one compound of Formula (I), or a pharmaceutically acceptable salt, solvate, ester, or prodrug of the compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula (I), or a pharmaceutically acceptable salt, solvate, ester, or prodrug of the compound and a pharmaceutically acceptable carrier, vehicle or diluent.

Yet another aspect of this invention is a kit comprising an amount of at least one compound of Formula (I), or a pharmaceutically acceptable salt, solvate, ester, or prodrug of the compound and an amount of at least one anticancer therapy and/or anti-cancer agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

The following solvents and reagents may be referred to by their abbreviations in parenthesis:
Thin layer chromatography: TLC
dichloromethane: CH$_2$Cl$_2$
ethyl acetate: AcOEt or EtOAc
methanol: MeOH
trifluoroacetate: TFA
triethylamine: Et$_3$N or TEA
butoxycarbonyl: n-Boc or Boc
nuclear magnetic resonance spectroscopy: NMR
liquid chromatography mass spectrometry: LCMS
high resolution mass spectrometry: HRMS
milliliters: mL
millimoles: mmol
microliters: μl
grams: g
milligrams: mg
room temperature or rt (ambient): about 25° C.
dimethoxyethane: DME In general, the compounds described in this invention can be prepared through the general routes described below in the Scheme 1 shown below.

Scheme 1

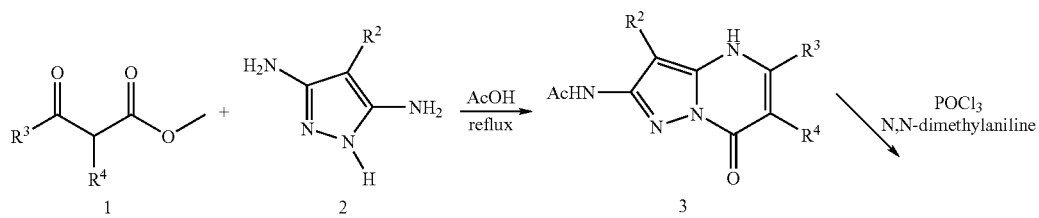

-continued

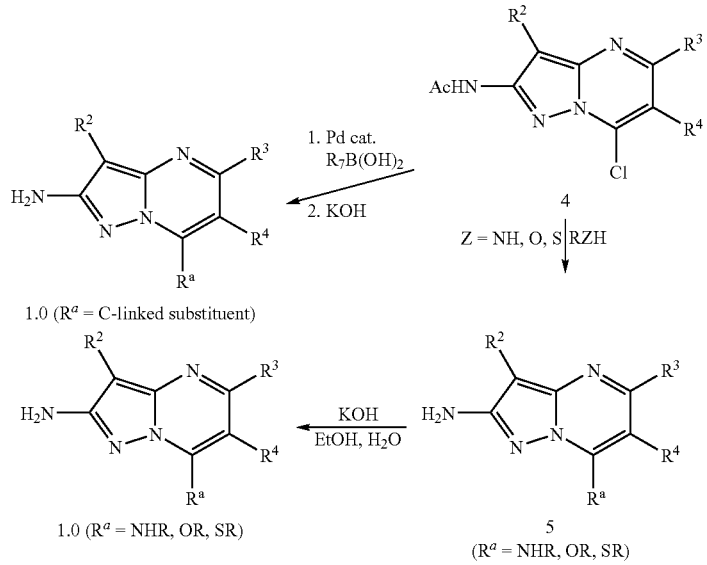

PREPARATIVE EXAMPLES AND EXAMPLES

Preparative Examples

Preparative Example 1

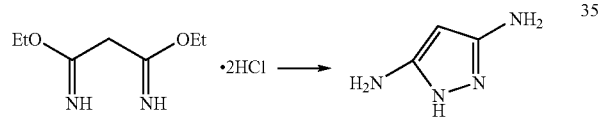

To a stirred suspension of diethyl malonimidate dichloride (23.1 g, 0.10 mol) in Et$_2$O was added at 0° C. aqueous saturated solution of K$_2$CO$_3$ (200 mL). The mixture was stirred under N$_2$ at 0° C. for 5 min, then separated in a separatory funnel, and the aqueous part was extracted with Et$_2$O (2×200 mL). The combined ether extracts were dried over Na$_2$SO$_4$, filtered, and the solvent was evaporated. The resulting colorless oil (14.9 g) was added in portions to a stirred boiling solution of 99% N$_2$H$_4$·H$_2$O (4.71 g, 94.3 mmol) in EtOH (45 mL), the mixture was stirred for 10 min and then kept at 4° C. for 16 hr. The solvent was evaporated and the residue was purified by column chromatography on silicagel with 4:1 CH$_2$Cl$_2$/7N NH$_3$ in MeOH as eluent. Pale yellow solid (4.40 g, 48%) was obtained.

Preparative Example 2

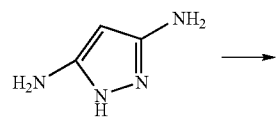

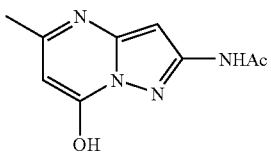

A mixture of the product from Preparative Example 1 (980 mg, 10.0 mmol) and ethyl benzoylacetate (2.20 g, 11.5 mmol) in AcOH (15 mL) was stirred and refluxed under N$_2$ for 5 hr. The mixture was cooled to 25° C., the solid was filtered off, washed on filter with AcOH (20 mL), Et$_2$O (40 mL), and dried in a vacuum. Cream-colored solid (930, 35%) was obtained. Mp>300° C. LC-MS: 269 [M+H].

Preparative Example 3

By essentially same procedure set forth in Preparative Example 2, compound given below was prepared from ethyl acetoacetate and compound from Preparative Example 1.

Mp>300° C. LC-MS: 207 [M+H].

Preparative Example 4

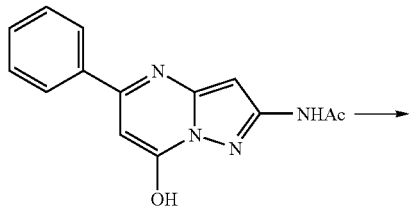

↓

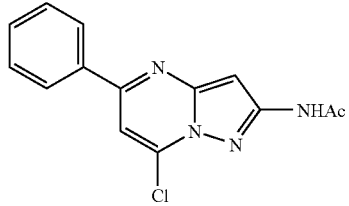

A mixture of the product from Preparative Example 2 (440 mg, 1.64 mmol), N,N-dimethylaniline (0.63 mL), and POCl$_3$ (5.0 mL) was stirred under N$_2$ at 25° C. for 4 d. The solvent was evaporated and the residue was purified by column chromatography on silicagel with 2:1 CH$_2$Cl$_2$/EtOAc as eluent. Pale yellow solid (225 mg, 48%) was obtained. LC-MS: 287 [M+].

Preparative Example 5

By essentially same procedure set forth in Preparative Example 4, compound given below was prepared.

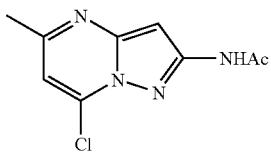

LC-MS: 225 [M+].

Preparative Example 6

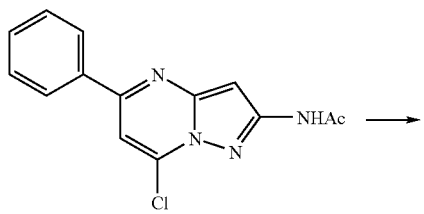

↓

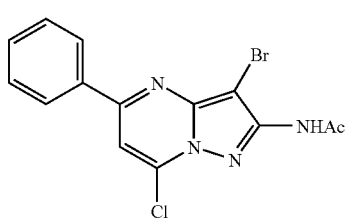

A solution of NBS (62 mg, 0.35 mmol) in anhydrous CH$_3$CN (3 mL) was added under N$_2$ to a stirred solution of the product from Preparative Example 4 (100 mg, 0.35 mmol) in anhydrous CH$_3$CN (3 mL) and CH$_2$Cl$_2$ (6 mL). The mixture was stirred for 2 hr, the solvents were evaporated, and the residue was purified by column chromatography on silicagel with 3:2 CH$_2$Cl$_2$/EtOAc as eluent. Pale yellow solid (52 mg, 41%) was obtained. LC-MS: 367 [M+H].

Preparative Example 7

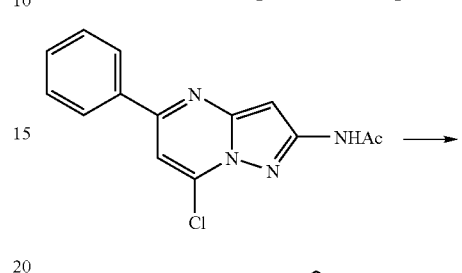

↓

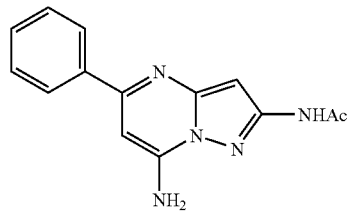

A mixture of the product from Preparative Example 4 (50 mg, 0.17 mmol), 2.0 M NH$_3$ in 2-propanol (2.0 mL), and conc. aqueous NH$_4$OH (0.2 mL) was stirred in a closed pressure vessel at 60° C. for 20 hr. The solvents were evaporated and the residue was purified by column chromatography on silicagel with 8:1 CH$_2$Cl$_2$/MeOH as eluent. Pale yellow solid (30 mg, 64%) was obtained.

Mp=258-260° C. LC-MS: 268 [M+H].

Preparative Example 8

By essentially same procedure set forth in Preparative Example 7, compound given below was prepared.

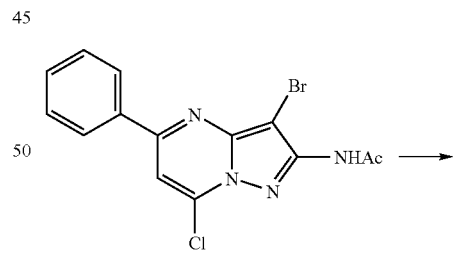

↓

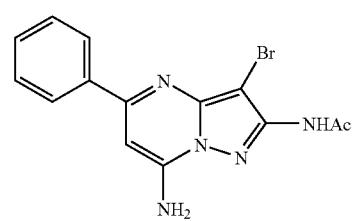

Mp=90-92° C. LC-MS: 346 [M+].

Preparative Example 9

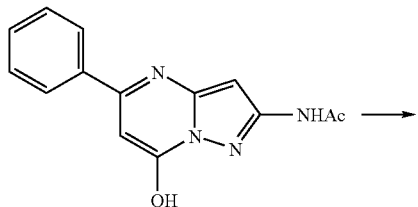

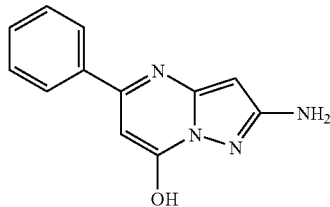

A mixture of the product from Preparative Example 2 (100 mg, 0.37 mmol) and KOH (200 mg), in EtOH (5 mL) and H$_2$O (1 mL) was stirred and refluxed under N$_2$ for 8 h. The solvent was evaporated and the residue was purified by column chromatography on silicagel with 5:1 CH$_2$Cl$_2$/MeOH as eluent. Pale yellow solid (6 mg, 7%) was obtained. Mp=175-177° C. LC-MS: 227 [M+H].

Preparative Example 10-11

By essentially same procedure set forth in Preparative Example 9, compounds given below were prepared.

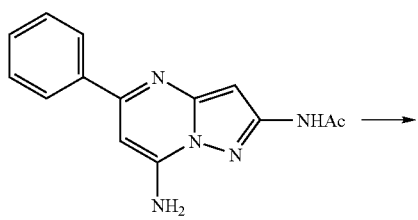

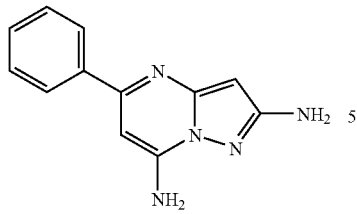

Mp=207-209° C. LC-MS: 227 [M+2H].

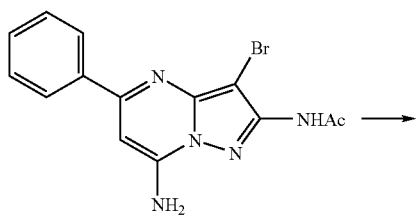

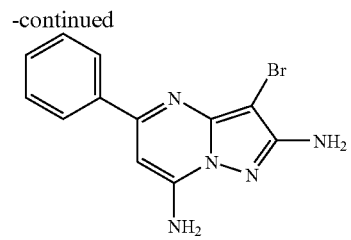

Mp=211-213° C. LC-MS: 306 [M+2H].

Preparative Example 12

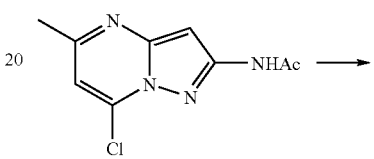

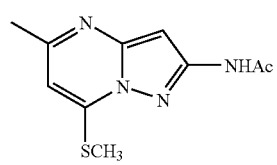

A mixture of the product from Preparative Example 5 (224 mg, 1.00 mmol) and sodium thiomethoxide (77 mg, 1.10 mmol) in THF (5 mL) was stirred at 25° C. under N$_2$ for 20 h. The solvent was evaporated and the residue was purified by column chromatography on silicagel with 10:1 CH$_2$Cl$_2$/MeOH as eluent. White solid (210 mg, 89%) was obtained. LC-MS: 237 [M+H].

EXAMPLES

Example 1

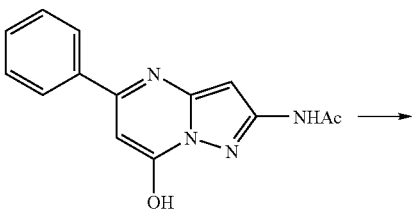

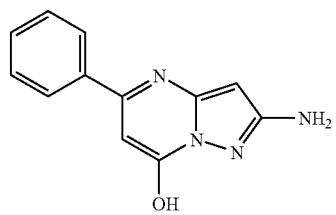

A mixture of the product from Preparative Example 2 (100 mg, 0.37 mmol) and KOH (200 mg), in EtOH (5 mL) and H$_2$O (1 mL) was stirred and refluxed under N$_2$ for 8 h. The solvent was evaporated and the residue was purified by column chromatography on silicagel with 5:1 CH$_2$Cl$_2$/MeOH as eluent.

Pale yellow solid (6 mg, 7%) was obtained. Mp=175-177° C. LC-MS: 227 [M+H].

Example 2

By essentially the same procedure set forth in Example 1, the compound given below was prepared.

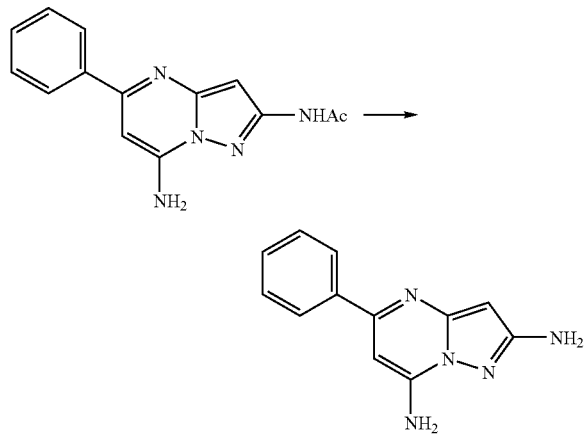

Mp=207-209° C. LC-MS: 227 [M+2H].

Example 3

By essentially the same procedure set forth in Example 1, the compound given below was prepared.

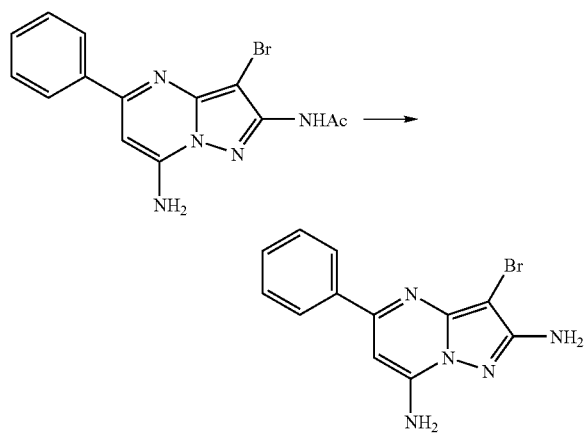

Mp=211-213° C. LC-MS: 306 [M+2H].

Assays:

CHK1 SPA Assay

An in vitro assay has been developed that utilizes recombinant His-CHK1 expressed in the baculovirus expression system as an enzyme source and a biotinylated peptide based on CDC25C as substrate (biotin-RSGLYR SPSMPENLNRPR).

Materials and Reagents:
1) CDC25C Ser 216 C-term Biotinylated peptide substrate (25 mg), stored at −20° C., Custom Synthesis by Research Genetics: biotin-RSGLYRSPSMPENLNRPR 2595.4 MW
2) His-CHK1 In House lot P976, 235 ug/mL, stored at −80° C.
3) D-PBS (without CaCl and MgCl): GIBCO, Cat.# 14190-144
4) SPA beads: Amersham, Cat.# SPQ0032: 500 mg/vial
   Add 10 mls of D-PBS to 500 mg of SPA beads to make a working concentration of 50 mg/ml. Store at 4° C. Use within 2 week after hydration.
5) 96-Well White Microplate with Bonded GF/B filter: Packard, Cat.# 6005177
6) Top seal-A 96 well Adhesive Film: Perkin Elmer, Cat.# 6005185
7) 96-well Non-Binding White Polystyrene Plate: Corning, Cat. # 6005177
8) $MgCl_2$: Sigma, Cat.# M-8266
9) DTT: Promega, Cat.# V3155
10) ATP, stored at 4° C.: Sigma, Cat.# A-5394
11) $\gamma^{33}$P-ATP, 1000-3000 Ci/mMol: Amersham, Cat.# AH9968
12) NaCl: Fisher Scientific, Cat.# BP358-212
13) $H_3PO_4$ 85% Fisher, Cat.#A242-500
14) Tris-HCL pH 8.0: Bio-Whittaker, Cat. # 16-015V
15) Staurosporine, 100 ug: CALBIOCHEM, Cat. # 569397
16) Hypure Cell Culture Grade Water, 500 mL: HyClone, Cat.# SH30529.02

Reaction Mixtures:
1) Kinase Buffer: 50 mM Tris pH 8.0; 10 mM $MgCl_2$; 1 mM DTT
2) His-CHK1, In House Lot P976, MW ~30 KDa, stored at −80° C.
   6 nM is required to yield positive controls of ~5,000 CPM. For 1 plate (100 rxn): dilute 8 uL of 235 ug/mL (7.83 uM) stock in 2 mL Kinase Buffer. This makes a 31 nM mixture. Add 20 uL/well. This makes a final reaction concentration of 6 nM.
3) CDC25C Biotinylated peptide.
   Dilute CDC25C to 1 mg/mL (385 uM) stock and store at −20° C. For 1 plate (100 rxn): dilute 10 uL of 1 mg/mL peptide stock in 2 ml Kinase Buffer. This gives a 1.925 uM mix. Add 20 uL/rxn. This makes a final reaction concentration of 385 nM.
4) ATP Mix.
   For 1 plate (100 rxn): dilute 10 uL of 1 mM ATP (cold) stock and 2 uL fresh P33-ATP (20 uCi) in 5 ml Kinase Buffer. This gives a 2 uM ATP (cold) solution; add 50 ul/well to start the reaction. Final volume is 100 ul/rxn so the final reaction concentrations will be 1 uM ATP (cold) and 0.2 uCi/rxn.
5) Stop Solution:
   For 1 plate add: To 10 mL Wash Buffer 2 (2M NaCl 1% $H_3PO_4$): 1 mL SPA bead slurry (50 mg); Add 100 uL/well
6) Wash buffer 1: 2 M NaCl
7) Wash buffer 2: 2 M NaCl, 1% $H_3PO_4$ Assay Procedure:

| Assay Component | Final Concentration | Volume |
| --- | --- | --- |
| CHK1 | 6 nM | 20 μl/rxn |
| Compound (10% DMSO) | — | 10 μl/rxn |

-continued

| Assay Component | Final Concentration | Volume |
|---|---|---|
| CDC25C | 0.385 μM | 20 μl/rxn |
| γ³³P-ATP | 0.2 μCi/rxn | 50 μl/rxn |
| Cold ATP | 1 μM | |
| Stop solution SPA beads | 0.5 mg/rxn | 100 μl/rxn* |
| | | 200 μl/rxn** |

*Total reaction volume for assay.
**Final reaction volume at termination of reaction (after addition of stop solution).

1) Dilute compounds to desired concentrations in water/10% DMSO—this will give a final DMSO concentration of 1% in the rxn. Dispense 10 □l/rxn to appropriate wells. Add 10 uL 10% DMSO to positive (CHK1+CDC25C+ATP) and negative (CHK1+ATP only) control wells.
2) Thaw enzyme on ice—dilute enzyme to proper concentration in kinase buffer (see Reaction Mixtures) and dispense 20 □l to each well.
3) Thaw the Biotinylated substrate on ice and dilute in kinase buffer (see Reaction Mixtures). Add 20 uL/well except to negative control wells. Instead, add 20 uL Kinase Buffer to these wells.
4) Dilute ATP (cold) and P33-ATP in kinase buffer (see Reaction Mixtures). Add 50 uL/well to start the reaction.
5) Allow the reaction to run for 2 hours at room temperature.
6) Stop reaction by adding 100 uL of the SPA beads/stop solution (see Reaction Mixtures) and leave to incubate for 15 minutes before harvest
7) Place a blank Packard GF/B filter plate into the vacuum filter device (Packard plate harvester) and aspirate 200 mL water through to wet the system.
8) Take out the blank and put in the Packard GF/B filter plate.
9) Aspirate the reaction through the filter plate.
10) Wash: 200 ml each wash; 1× with 2M NaCl; 1× with 2M NaCl/1% $H_3PO_4$
11) Allow filter plate to dry 15 min.
12) Put TopSeal-A adhesive on top of filter plate.
13) Run filter plate in Top Count
    Settings: Data mode: CPM
    Radio nuclide: Manual SPA:P33
    Scintillator: Liq/plast
    Energy Range: Low CDK2 Assay:

BACULOVIRUS CONSTRUCTIONS: Cyclins A and E were cloned into pFASTBAC (Invitrogen) by PCR, with the addition of a GluTAG sequence (EYMPME) at the amino-terminal end to allow purification on anti-GluTAG affinity columns. The expressed proteins were approximately 46 kDa (cyclin E) and 50 kDa (cyclin A) in size. CDK2 was also cloned into pFASTBAC by PCR, with the addition of a haemaglutinin epitope tag at the carboxy-terminal end (YD-VPDYAS). The expressed protein was approximately 34 kDa in size.

ENZYME PRODUCTION: Recombinant baculoviruses expressing cyclins A, E and CDK2 were infected into SF9 cells at a multiplicity of infection (MOI) of 5, for 48 hrs. Cells were harvested by centrifugation at 1000 RPM for 10 minutes. Cyclin-containing (E or A) pellets were combined with CDK2 containing cell pellets and lysed on ice for 30 minutes in five times the pellet volume of lysis buffer containing 50 mM Tris pH 8.0, 0.5% NP40, 1 mM DTT and protease/phosphatase inhibitors (Roche Diagnostics GmbH, Mannheim, Germany). Mixtures were stirred for 30-60 minutes to promote cyclin-CDK2 complex formation. Mixed lysates were then spun down at 15000 RPM for 10 minutes and the supernatant retained. 5 ml of anti-GluTAG beads (for one liter of SF9 cells) were then used to capture cyclin-CDK2 complexes. Bound beads were washed three times in lysis buffer. Proteins were competitively eluted with lysis buffer containing 100-200 ug/mL of the GluTAG peptide. Eluate was dialyzed overnight in 2 liters of kinase buffer containing 50 mM Tris pH 8.0, 1 mM DTT, 10 mM MgCl2, 100 uM sodium orthovanadate and 20% glycerol. Enzyme was stored in aliquots at −70° C.

IN VITRO KINASE ASSAY: CDK2 kinase assays (either cyclin A or E-dependent) were performed in low protein binding 96-well plates (Corning Inc, Corning, N.Y.). Enzyme was diluted to a final concentration of 50 μg/ml in kinase buffer containing 50 mM Tris pH 8.0, 10 mM $MgCl_2$, 1 mM DTT, and 0.1 mM sodium orthovanadate. The substrate used in these reactions was a biotinylated peptide derived from Histone H1 (from Amersham, UK). The substrate was thawed on ice and diluted to 2 μM in kinase buffer. Compounds were diluted in 10% DMSO to desirable concentrations. For each kinase reaction, 20 μl of the 50 μg/ml enzyme solution (1 μg of enzyme) and 20 μl of the 1 μM substrate solution were mixed, then combined with 10 μl of diluted compound in each well for testing. The kinase reaction was started by addition of 50 μl of 4 μM ATP and 1 μCi of 33P-ATP (from Amersham, UK). The reaction was allowed to run for 1 hour at room temperature. The reaction was stopped by adding 200 μl of stop buffer containing 0.1% Triton X-100, 1 mM ATP, 5 mM EDTA, and 5 mg/ml streptavidine coated SPA beads (from Amersham, UK) for 15 minutes. The SPA beads were then captured onto a 96-well GF/B filter plate (Packard/Perkin Elmer Life Sciences) using a Filtermate universal harvester (Packard/Perkin Elmer Life Sciences.). Non-specific signals were eliminated by washing the beads twice with 2M NaCl then twice with 2 M NaCl with 1% phosphoric acid. The radioactive signal was then measured using a TopCount 96 well liquid scintillation counter (from Packard/Perkin Elmer Life Sciences).

$IC_{50}$ DETERMINATION: Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis. The thus-obtained $IC_{50}$ values for selected compounds of the invention are shown in Table 1 above. These kinase activities were generated by using the above-described assay.

As demonstrated above by the assay values, the compounds of the present invention can exhibit good Chk1 inhibitory properties.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound represented by the structural formula (I):

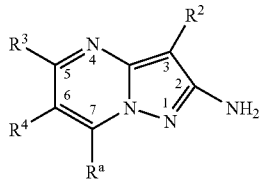
(I)

or a pharmaceutically acceptable salt of the compound of formula (I), wherein:

R$^2$ is selected from the group consisting of H, alkyl, cycloalkyl, cycloalkylalkyl, haloalkyl, alkenyl, alkynyl, alkenylalkyl, alkynylalkyl, heterocyclyl, heterocycloalkyl, trifluoromethyl, halo, —OCF$_3$, —CO$_2$R$^8$, —CONR$^8$R$^9$, —OR$^{8a}$, —SR$^8$, —SO$_2$R$^8$, —SO$_2$NR$^8$R$^9$, —NR$^8$SO$_2$R$^9$, —NR$^8$COR$^9$, and —NR$^8$CONR$^8$R$^9$;

R$^3$ is selected from the group consisting of haloalkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl, —NR$^5$R$^{8a}$, —NR$^8$COR$^9$, —NR$^8$SO$_2$R$^9$, —COR$^8$, —CO$_2$R$^8$, —CONR$^8$R$^9$, —CH$_2$OR$^8$, —OR$^{8b}$, —SR$^8$, —SO$_2$R$^8$, —S(O$_2$)NR$^8$R$^9$, —S(O$_2$)aryl, —S(O$_2$)heteroaryl, —C(O)NR$^8$R$^9$, —C(O)OR$^9$, —C(O)aryl, —C(O)heteroaryl, —(CHR$^5$)$_n$-aryl, —(CHR$^5$)$_n$-heteroaryl,

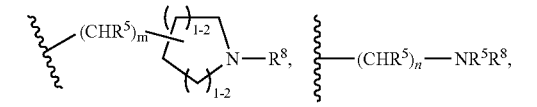

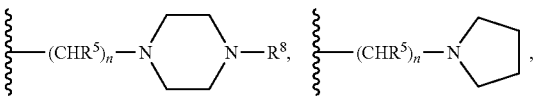

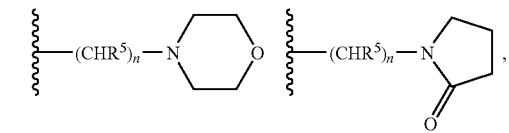

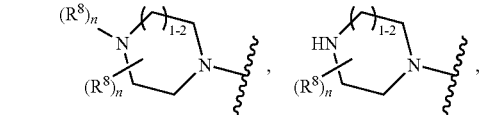

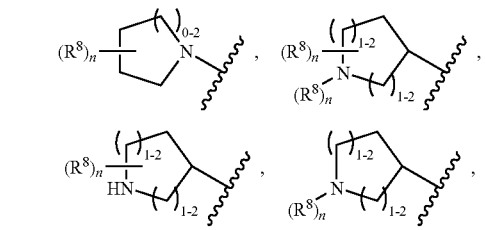

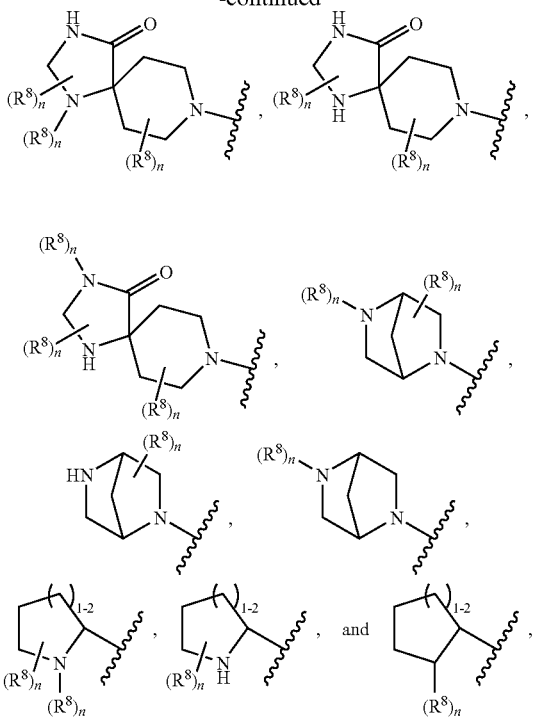

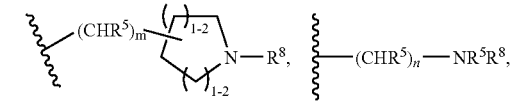

wherein each of the alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl and the heterocyclic moieties shown immediately above for R$^3$ can be unsubstituted or optionally substituted with one or more moieties which can be the same or different, each moiety being independently selected from the group consisting of H, halo, alkyl, trifluoromethyl, —OR$^8$, —NR$^8$R$^9$, —SR$^8$, —SO$_2$R$^9$, —CN, —SO$_2$NR$^8$R$^9$, —CF$_3$, and —NO$_2$.;

R$^4$ is selected from the group consisting of H, halo, haloalkyl, alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl, —NR$^8$R$^9$, —NR$^8$COR$^9$, —NR$^8$SO$_2$R$^9$, —COR$^8$, —CO$_2$R$^8$, —CONR$^8$R$^9$, —CH$_2$OR$^8$, —OR$^8$, —SR$^8$, —SO$_2$R$^8$, —S(O$_2$)NR$^8$R$^9$, —S(O$_2$)aryl, —S(O$_2$)heteroaryl, —C(O)OR$^9$, —C(O)aryl, —C(O)heteroaryl, —(CHR$^5$)$_n$-aryl, —(CHR$^5$)$_n$-heteroaryl,

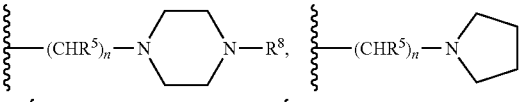

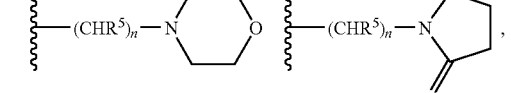

-continued

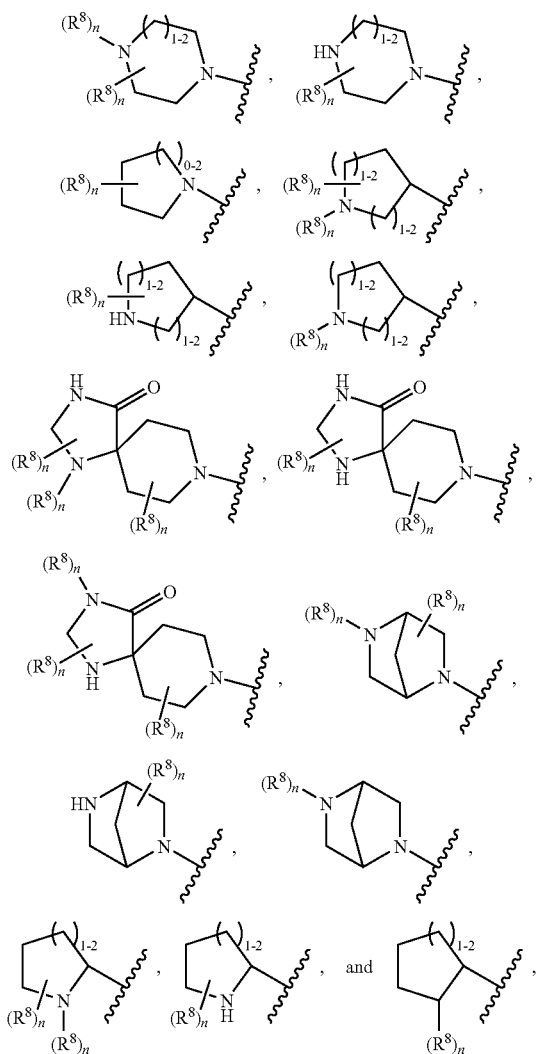

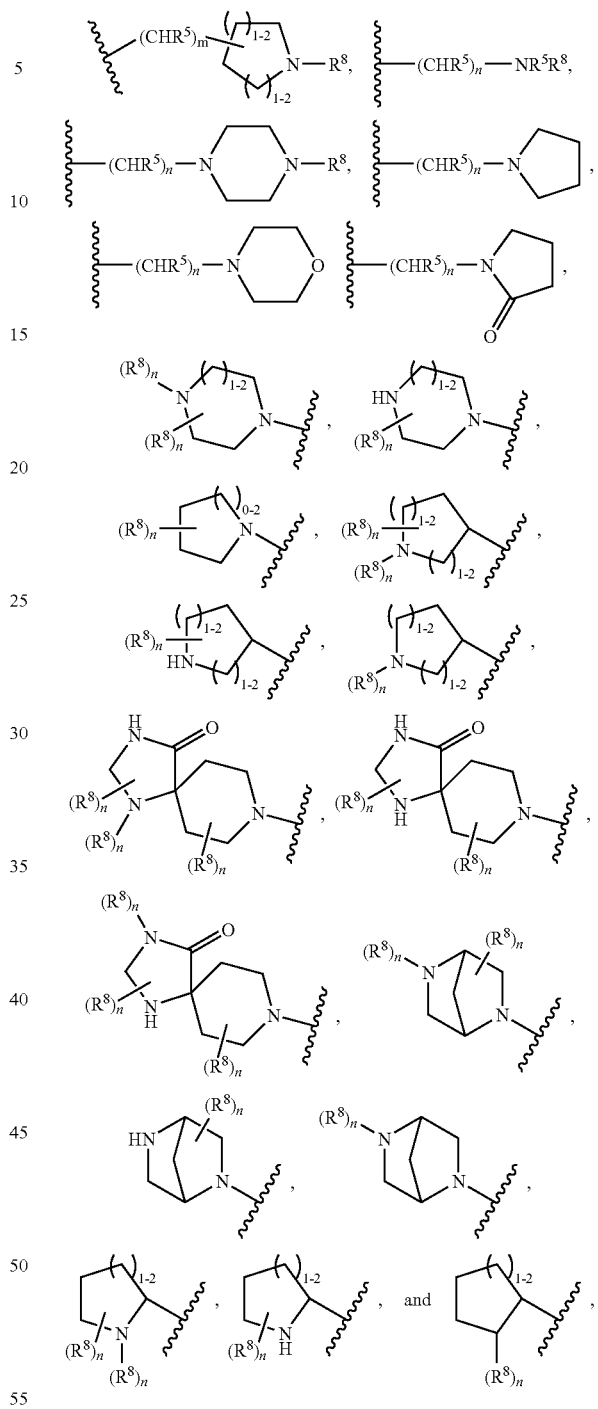

wherein each of the alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl and the heterocyclic moieties shown immediately above for $R^4$ can be unsubstituted or optionally substituted with one or more moieties which can be the same or different, each moiety being independently selected from the group consisting of H, halo, alkyl, trifluoromethyl, —$OR^8$, —$NR^8R^9$, —$SR^8$, —$SO_2R^9$, —CN, —$SO_2NR^8R^9$, —$CF_3$, and —$NO_2$;

$R^a$ is selected from the group consisting of H, halo, haloalkyl, alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroarylalkyl, —$NR^8R^9$, —$NR^8COR^9$, —$NR^8SO_2R^9$, —$COR^8$, —$CO_2R^8$, —$CONR^8R^9$, —$CH_2OR^8$, —$OR^8$, —$SR^8$, —$SO_2R^8$, —$S(O_2)NR^8R^9$, —$S(O_2)$aryl, —$S(O_2)$heteroaryl, —$C(O)OR^9$, —$C(O)$aryl, —$C(O)$heteroaryl, —$(CHR^5)_n$-aryl, —$(CHR^5)_n$-heteroaryl, wherein each of the alkyl, alkenyl, alkynyl, aryl, arylalkyl, arylalkenyl, cycloalkyl, cycloalkylalkyl, alkenylalkyl, alkynylalkyl, heterocyclyl, heterocyclylalkyl, heteroaryl, heteroaryl alkyl and the heterocyclic moieties shown immediately above for $R^a$ can be unsubstituted or optionally substituted with one or more moieties which can be the same or different, each moiety being independently selected from the group consisting of H, halo, alkyl, trifluoromethyl, —$OR^8$, —$NR^8R^9$, —$SR^8$, —$SO_2R^9$, —CN, —$SO_2NR^8R^9$, —$CF_3$, and —$NO_2$;

R⁵ is selected from the group consisting of H, alkyl, aryl or cycloalkyl;

R⁶ is selected from the group consisting of H, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —CF₃, —OCF₃, —CN, —OR⁵, —NR⁵R¹⁰, —(CR⁵R¹¹)$_p$—R⁹, —N(R⁵)(Butoxycarbonyl), —(CR⁵R¹¹)$_p$OR⁵, —C(O₂)R⁵, —C(O)R⁵, —C(O)NR⁵R¹⁰, —SO₃H, —SR¹⁰, —S(O₂)R⁷, —S(O₂)NR⁵R¹⁰, —N(R⁵)S(O₂)R⁷, —N(R⁵)C(O)R⁷ and —N(R⁵)C(O)NR⁵R¹⁰;

R⁷ is selected from the group consisting of alkyl, cycloalkyl, aryl, arylalkenyl, heteroaryl, arylalkyl, heteroarylalkyl, heteroarylalkenyl, and heterocyclyl, wherein each of the alkyl, cycloalkyl, heteroarylalkyl, aryl, arylalkenyl, heteroaryl, arylalkyl, heteroarylalkyl, heteroarylalkenyl, and heterocyclyl can be unsubstituted or optionally independently substituted with one or more moieties which can be the same or different, each moiety being independently selected from the group consisting of halo, alkyl, aryl, cycloalkyl, CF₃, OCF₃, CN, —OR⁵, —NR⁵R¹⁰, —CH₂OR⁵, —C(O₂)R⁵, —C(O)NR⁵R¹⁰, —C(O)R⁵, —SR¹⁰, —S(O₂)R¹⁰, —S(O₂)NR⁵R¹⁰, —N(R⁵)S(O₂)R¹⁰, —N(R⁵)C(O)R¹⁰ and —N(R⁵)C(O)NR⁵R¹⁰;

R⁸ is selected from the group consisting of H, —OR⁶, —NR⁵R⁶, —C(O)NR⁵R¹⁰, —S(O₂)NR⁵R¹⁰, —C(O)R⁷, —C(═N—CN)—NH₂, —C(═NH)—NHR⁵, heterocyclyl, —S(O₂)R⁷,

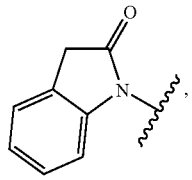

—OR¹⁰, —CF₃, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —CF₃, —OCF₃, —CN, —OR⁵, —NR⁵R¹⁰, —(CR⁵R¹¹)$_p$—R⁹, —N(R⁵)(Butoxycarbonyl), —(CR⁵R¹¹)$_p$OR⁵, —C(O₂)R⁵, —C(O)R⁵, —C(O)NR⁵R¹⁰, —SO₃H, —SR¹⁰, —S(O₂)R⁷, —S(O₂)NR⁵R¹⁰, —N(R⁵)S(O₂)R⁷, —N(R⁵)C(O)R⁷ and —N(R⁵)C(O)NR⁵R¹⁰;

R⁸ᵃ is selected from the group consisting of —OR⁶, —NR⁵R⁶, —C(O)NR⁵R¹⁰, —S(O₂)NR⁵R¹⁰, —C(O)R⁷, —C(═N—CN)—NH₂, —C(═NH)—NHR⁵, heterocyclyl, —S(O₂)R⁷,

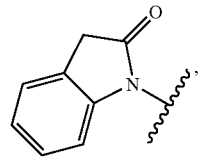

—OR¹⁰, —CF₃, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —CF₃, —OCF₃, —CN, —OR⁵, —NR⁵R¹⁰, —(CR⁵R¹¹)$_p$—R⁹, —N(R⁵)Butoxycarbonyl), —(CR⁵R¹¹)$_p$OR⁵, —C(O₂)R⁵, —C(O)R⁵, —C(O)NR⁵R¹⁰, —SO₃H, —SR¹⁰, —S(O₂)R⁷, —S(O₂)NR⁵R¹⁰, —N(R⁵)S(O₂)R⁷, —N(R⁵)C(O)R⁷ and —N(R⁵)C(O)NR⁵R¹⁰;

R⁸ᵇ is selected from the group consisting of —OR⁶, —NR⁵R⁶, —C(O)NR⁵R¹⁰, —S(O₂)NR⁵R¹⁰, —C(O)R⁷, —C(═N—CN)—NH₂, —C(═NH)—NHR⁵, heterocyclyl, —S(O₂)R⁷,

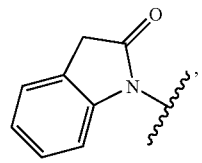

—OR¹⁰, —CF₃, alkenyl, aryl, arylalkyl, arylalkenyl, cycloalkyl, heterocyclyl, heterocyclylalkyl, heteroaryl, and heteroarylalkyl, wherein each of the alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —CF₃, —OCF₃, —CN, —OR⁵, —NR⁵R¹⁰, —(CR⁵R¹¹)$_p$—R⁹, —N(R⁵)(Butoxycarbonyl), —(CR⁵R¹¹)$_p$OR⁵, —C(O₂)R⁵, —C(O)R⁵, —C(O)NR⁵R¹⁰, —SO₃H, —SR¹⁰, —S(O₂)R⁷, —S(O₂)NR⁵R¹⁰, —N(R⁵)S(O₂)R⁷, —N(R⁵)C(O)R⁷ and —N(R⁵)C(O)NR⁵R¹⁰;

R⁹ is selected from the group consisting of H, —OR⁶, —NR⁵R⁶, —C(O)NR⁵R¹⁰, —S(O₂)NR⁵R¹⁰, —C(O)R⁷, —C(═N—CN)—NH₂, —C(═NH)—NHR⁵, heterocyclyl, —S(O₂)R⁷,

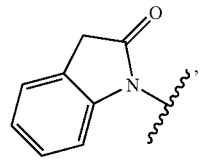

—OR¹⁰, —CF₃, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —$CF_3$, —$OCF_3$, —CN —$OR^5$, —$NR^5R^{10}$, —$N(R^5)$(Butoxycarbonyl), —$(CR^5R^{11})_p$ $OR^5$, —$C(O_2)R^5$, —$C(O)R^5$, —$C(O)NR^5R^{10}$, —$SO_3H$, —$SR^{10}$, —$S(O_2)R^7$, —$S(O_2)NR^5R^{10}$, —$N(R^5)S(O_2)R^7$, —$N(R^5)C(O)R^7$ and —$N(R^5)C(O)NR^5R^{10}$;

$R^{10}$ is selected from the group consisting of H, alkyl, alkenyl, aryl, arylalkyl, arylalkenyl, cycloalkyl, heterocyclyl, heterocyclylalkyl, heteroaryl, and heteroarylalkyl, wherein each of the alkyl, alkenyl, aryl, arylalkyl, cycloalkyl, heterocyclyl, heterocyclylalkyl, heteroaryl, and heteroarylalkyl groups can be unsubstituted or optionally substituted with one or more moieties which can be the same or different, each moiety being independently selected from the group consisting of halo, alkyl, aryl, cycloalkyl, heterocyclylalkyl, —$CF_3$, —$OCF_3$, —CN, —$OR^5$, —$NR^5R^{11}$, —$(CR^5R^{11})_p$—$R^9$, —$N(R^5)$ Butoxcarbonyl, —$(CR^5R^{11})_pOR^5$, —$C(O_2)R^5$, —$C(O)R^5$, —$C(O)NR^5R^1$, —$SO_3H$, —$SR^{11}$, —$S(O_2)R^7$, —$S(O_2)NR^5R^{11}$, —$N(R^5)S(O_2)R^7$, —$N(R^5)C(O)R^7$ and —$N(R^5)C(O)NR^5R^{11}$;

or optionally (i) $R^5$ and $R^{11}$ in the moiety —$NR^5R^{11}$, or (ii) $R^5$ and $R^6$ in the moiety —$NR^5R^6$, may be joined together to form a heterocyclyl moiety, with the heterocyclyl moiety being unsubstituted or optionally independently being substituted with one or more $R^9$ groups; and $R^{11}$ is H, halo or alkyl;

m is 0 to 4;

n is 1 to 4; and p is 1 to 4;

with the following provisos:

(a) when $R^4$ and $R^a$, are selected from the group consisting of —$NH_2$, —OH, alkynyl, alkenylalkyl, and alkynylalkyl, then $R^2$ is selected from the group consisting of alkyl, cycloalkyl, cycloalkylalkyl, haloalkyl, alkenyl, alkynyl, alkenylalkyl, alkynylalkyl, trifluoromethyl, —$OCF_3$, —$OR^{8a}$, —$SR^8$, and —$NR^8CONR^8R^9$.

2. The compound according to claim 1, wherein $R^2$ is H.

3. The compound according to claim 1, wherein $R^2$ is Br.

4. The compound according to claim 1, wherein $R^2$ is selected from the group consisting of Cl, —SH, —CN, alkyl, alkenyl, alkynyl, and cyclopropyl.

5. The compound according to claim 1, wherein $R^2$ is selected from the group consisting of cycloalkyl, cycloalkylalkyl, heterocyclyl, heterocycloalkyl, —$OCF_3$, —$CO_2R^8$, —$CONR^8R^9$, —$OR^{8a}$, —$SR^8$, —$SO_2R^8$, —$SO_2NR^8R^9$, —$NR^8SO_2R^9$, —$NR^8COR^9$, and —$NR^8CONR^8R^9$.

6. The compound according to claim 1, wherein $R^3$ is benzyl.

7. The compound according to claim 1, wherein $R^3$ is selected from the group consisting of aryl, arylalkyl, arylalkenyl, cycloalkyl, cycloalkylalkyl, heterocyclyl, heterocyclylalkyl, heteroaryl, heteroarylalkyl, —$S(O_2)$aryl, —$S(O_2)$heteroaryl, —C(O)aryl, —C(O)heteroaryl, —$(CHR^5)_n$-aryl, —$(CHR^5)_n$-heteroaryl,

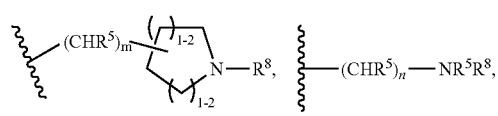

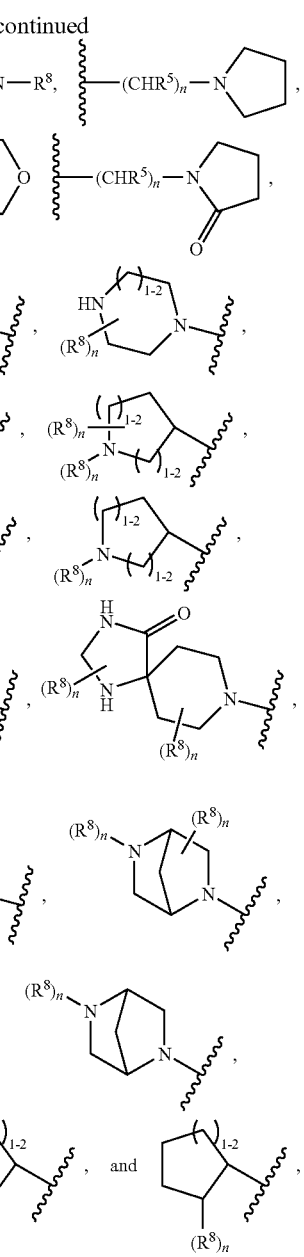

wherein each of the aryl, arylalkyl, arylalkenyl, cycloalkyl, cycloalkylalkyl, heterocyclyl, heterocyclylalkyl, heteroaryl, heteroarylalkyl and the heterocyclic moieties shown immediately above for $R^3$ can be unsubstituted or optionally substituted with one or more moieties which can be the same or different, each moiety being independently selected from the group consisting of H, halo, alkyl, trifluoromethyl, —$OR^8$, —$NR^8R^9$, —$SR^8$, —$SO_2R^9$, —CN, —$SO_2NR^8R^9$, —$CF_3$, and —$NO_2$.

8. The compound according to claim 1, wherein $R^3$ is selected from the group consisting of haloalkyl, alkenyl, alkynyl, alkenylalkyl, alkynylalkyl, —$NR^5R^{8a}$, —$NR^8COR^9$, —$NR^8SO_2R^9$, —$COR^8$, —$CO_2R^8$, —$CONR^8R^9$, —$CH_2OR^8$, —$OR^{8b}$, —$SR^8$, —$SO_2R^8$, —$S(O_2)NR^8R^9$, wherein each of the alkenyl, alkynyl, alkenylalkyl, alkynylalkyl, can be unsubstituted or optionally substituted with one or more moieties which can be the same or different, each moiety being independently selected from the group consisting of H, halo, alkyl, trifluoromethyl, —OR$^8$, —NR$^8$R$^9$, —SR$^8$, —SO$_2$R$^9$, —CN, —SO$_2$NR$^8$R$^9$, —CF$_3$, and —NO$_2$.

9. The compound according to claim 1, wherein R$^3$ is OR$^{8b}$.

10. The compound according to claim 1, wherein R$^3$ is alkylthio.

11. The compound according to claim 1, wherein R$^3$ is selected from the group consisting of

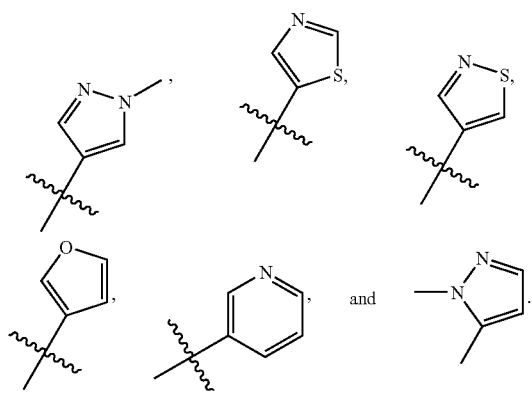

12. The compound according to claim 1, wherein R$^3$ is selected from the group consisting of heteroaryl, heteroarylalkyl, heterocyclyl and heterocyclylalkyl.

13. The compound according to claim 1, wherein R$^4$ is H.

14. The compound according to claim 1, wherein R$^4$ is selected from the group consisting of Cl, Br, —OH, —SH, alkyl, alkenyl, alkynyl, haloalkyl and cyclopropyl.

15. The compound according to claim 1, wherein R$^4$ is —NH$_2$.

16. The compound according to claim 1, wherein R$^4$ is —OH.

17. The compound according to claim 1, wherein R$^4$ is alkoxy.

18. The compound according to claim 1, wherein R$^4$ is alkylthio.

19. The compound according to claim 1, wherein R$^4$ is halo.

20. The compound according to claim 1, wherein R$^a$ is —NH$_2$.

21. The compound according to claim 1, wherein R$^a$ is —OH.

22. The compound according to claim 1, wherein R$^a$ is alkoxy.

23. The compound according to claim 1, wherein R$^a$ is alkylthio.

24. The compound according to claim 1, wherein R$^a$ is halo.

25. The compound according to claim 1, wherein R$^a$ is Cl.

26. The compound according to claim 1, wherein R$^5$ is H.

27. The compound according to claim 1, wherein n is 1.

28. The compound according to claim 1, wherein p is 1.

29. The compound according to claim 1, wherein the compound is selected from the group consisting of:

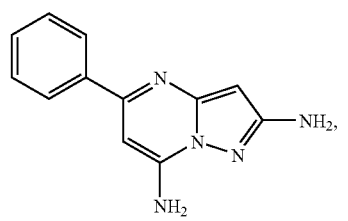

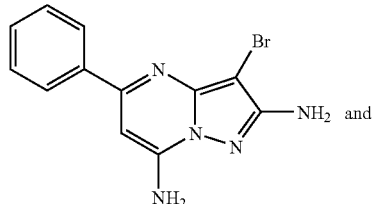

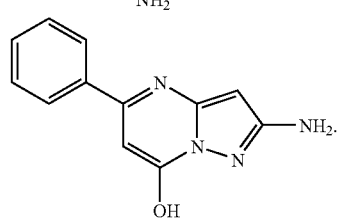

30. A compound according to claim 1 or a pharmaceutically acceptable salt thereof in purified and isolated form.

31. A pharmaceutical composition comprising a therapeutically effective amount of at least one compound of claim 1 or a pharmaceutically acceptable salt thereof, in combination with at least one pharmaceutically acceptable carrier.

* * * * *

UNITED STATES PATENT AND TRADEMARK OFFICE
CERTIFICATE OF CORRECTION

PATENT NO.        : 7,645,762 B2
APPLICATION NO.   : 11/542902
DATED             : January 12, 2010
INVENTOR(S)       : Kamil Paruch et al.

It is certified that error appears in the above-identified patent and that said Letters Patent is hereby corrected as shown below:

In the Claims:

Claim 1, col. 42, line 32:   Please delete "alkyl".

Claim 1, col. 47, line 21:   Please replace "Butoxycarbonyl" with "-(Butoxycarbonyl)".

Claim 1, col. 47, line 46:   Please delete "-CN".

Signed and Sealed this

Thirty-first Day of August, 2010

David J. Kappos
*Director of the United States Patent and Trademark Office*